United States Patent [19]

Calenoff

[11] Patent Number: 4,675,286

[45] Date of Patent: Jun. 23, 1987

[54] FETAL CELL SEPARATION AND TESTING

[75] Inventor: Emanuel Calenoff, San Francisco, Calif.

[73] Assignee: Aspen Diagnostics, Inc., Palo Alto, Calif.

[21] Appl. No.: 695,971

[22] Filed: Jan. 28, 1985

[51] Int. Cl.[4] .................. A61B 10/00; G01N 33/543; G01N 33/554; G01N 33/577

[52] U.S. Cl. ........................................ 435/7; 128/749; 128/750; 435/30; 435/172.2; 435/240; 436/177; 436/178; 436/518; 436/519; 436/526; 436/527; 436/531; 436/548; 436/825; 436/828; 530/387; 530/808; 935/108

[58] Field of Search ............... 436/518, 824, 519, 177, 436/178, 825; 435/30, 7; 128/749, 750

[56] References Cited

U.S. PATENT DOCUMENTS 4,100,923  7/1978  Southern ............................... 605/55
4,194,513  3/1980  Rhine ................................... 128/750

OTHER PUBLICATIONS

Anonymous, Chinese Med. Journ. 1, 117–126, 1975.
W. P. Clark, *The Experimental Foundations of Modern Immunology*, 2nd Ed., John Wiley & Sons, New York, 1983, p. 304.
G. M. Edelman et al, *Meth. Enzymol.*, 34, 195–225, 1974.
L. A. Merzenberg et al, in D. M. Weir (Ed.), *Handbook of Experimental Immunology*, 3rd Edition, Blackwell Scientific Pub., Oxford, 1978, pp. 22.1–22.20.
P. M. Johnson et al, *Journ. Immunol.*, 132, 1608–1610, 1984.
M. Kawata et al, *Journ. Exp. Md.*, 160, 633–651, 1984.
B. Montgomery et al, *Journ. Immunol.*, 131, 2348–2355, 1984.
I. M. Roitt, *Essential Immunology*, 5th Edition, Blackwell Scientific Pub., Oxford, 1984, pp. 271–279.
Blumer and Johnson, Placenta, 6:127–140 (1985).
Johnson, et al, *Journal of Reproductive Immunology*, 4:1–9 (1982).
Boyd, et al, *The Human Placenta*, Cambridge: The Macmillan Press (1970).

*Primary Examiner*—Sidney Marantz
*Assistant Examiner*—David A. Saunders
*Attorney, Agent, or Firm*—William B. Walker

[57] ABSTRACT

A method for obtaining fetal cells for diagnostic examination comprises removing detached cells from the uterine cavity and outer surface of the amnionic sac. The cells are then incubated in the presence of a separation antibody which binds preferentially to either fetal cell antigens or maternal cell antigens for a time sufficient to permit antibody-antigen binding to occur. Cells having said separation antibody bound thereto are separated for the mixture. The separation antibody can be an anitbody binding preferentially to fetal cell antigens and not significantly to maternal cell antigens or it can be an antibody binding preferentially to maternal cell antigens and not significantly to fetal cell antigens. The antibody can be bound to an insoluble support prior to the incubation, and separation can be effected by separating the insoluble support from the cell mixture following the incubation. Alternatively, the separation antibody can be fluorescent labeled, and cells conjugated with fluorescent labeled antibody can be removed using a cell sorter. The isolated fetal cells are then propagated to obtain a population sufficient for diagnostic examination.

6 Claims, No Drawings

FETAL CELL SEPARATION AND TESTING

FIELD OF THE INVENTION

This invention relates to a method for separating, propagating and testing fetal cells. In particular, this invention relates to the separation of fetal cells from mixtures of fetal and maternal cells obtained from areas between the walls of the uterine cavity and the external surface of the amnionic sac, and the propagation of these cells for testing.

BACKGROUND OF THE INVENTION

The examination of fetal cells for early detection of fetal diseases and genetic abnormalities is frequently undertaken when abnormalities are suspected. The fetal cells for this examination are usually obtained by amniocentesis, the removal of amnionic fluid directly from the amnionic cavity within the amnionic sac or placenta. In this procedure a hollow tube is inserted through the wall of the amnionic sac. Even with the use of ultrasound imaging techniques to monitor the relative positions of the tube and the fetus, risk of harm to the fetus is a matter of concern. Particularly after the first trimester of pregnancy, safe removal of amnionic fluid becomes more difficult. As a consequence, examination of fetal cells for early detection of abnormalities has not been established as a routine procedure for all pregnancies. Detectable genetic abnormalities and diseases often remain undetected until birth.

DESCRIPTION OF THE PRIOR ART

The propagation and examination of fetal cells obtained by amniocenteses has been widely described, for example by M. Golbus, et al. Prenatal genetic diagnosis in 3000 amniocenteses. *New England Journal of Medicine.* 300:157–163 (1979) and the citations therein.

That the tissue of the placenta includes both fetal and maternal cells has been confirmed by M. Kawata et al, Transcriptional control of HLA-A,B,C antigen in human placental cytotrophoblast isolated using trophoblast - and HLA-specific monoclonal antibodies and the fluorescence-activated cell sorter in *J. Exp. Med.* 160:633–651 (1984). The presence of HLA-A,B,C and beta-2-microglobulin (beta-2-m) antigens on the maternal cells but not on the trophoblasts from placentas obtained from uncomplicated deliveries and Caesarian sections at term was determined using HLA-A,B,C specific and beta-2-m antibodies. Use of anti-Trop-1 and anti-Trop-2 antibodies (fetal trophoblast cell surface antigen specific antibodies) in staining placental tissue was also described. Related research is reported by Hsi, B. et al. *Immunology (England).* 52(4):621–629 (Aug. 1984); Redman, C. et al. *Immunology (England).* 52(3):457–468 (Jul. 1984); Johnson, P. et al. *J. Immunol.* 132(4):1608–1610 (Apr. 1984); Montgomery, B. et al. *J. Immunol.* 131(5):2348–2355 (1983); Faulk, W. *Int. J. Tissue React.* (Switzerland). 3(3–4):139–146 (1981); and Sunderland, C. et al. *J. Immunol.* 127(6):2614–2615 (1981).

Confirmation of cytogenetically abnormal fetuses following saline abortions was shown to be possible using fetal cells derived from the placenta by Gardner, H. A. et al. Placental cultures for cytogenetic assessment in saline aborted fetuses. *Am. J. Obstet. Gynecol.* 126(3):350–352 (1976). Detailed examination of the stained chromosomes for polymorphisms was used to distinguish female fetal tissue from maternal tissue.

Use of antibodies specific for cell surface markers to effect separation of cells has been described by R. Mishell et al. in SELECTED METHODS IN CELLULAR IMMUNOLOGY. San Francisco: Freeman, pp 209–234 (1980) and Pretlow et al. (editors) CELL SEPARATION METHODS AND SELECTED APPLICATIONS. New York: Academic Press. (1982). Use of cell antigen binding antibodies which have been labeled with fluorescein to mark cells for cell sorter separation has been described by L. Herzenberg et al. HANDBOOK OF EXPERIMENTAL IMMUNOLOGY. London: Blackwell Scientific, pp 22.1–22.21 (1978).

Antibodies have been adhered to numerous solid supports by both physical and chemical bonding. Antibodies have been bonded to insoluble supports as described in U.S. Pat. Nos. 3,551,555, 3,553,310, 4,048,298 and RE-29,474, for example. Binding of antibodies to polystyrene supports by adsorption has been described in U.S. Pat. Nos. 3,646,346 and 4,092,408, for example. Adhering biological materials to solid, magnetic particles is described by U.S. Pat. Nos. 3,933,997, 3,985,649, 4,177,253 and 4,297,337, for example. Coating magnetic particles with antibodies for separating selected cells from mixtures has been described in U.S. Pat. No. 3,970,518. Cell separation using coated magnetic materials are described by Antoine, J. et al. *Immunochemistry.* 15:443–452 (1978); Ghelie, V. et al. *Scand. J. Immunol.* 4:471–477 (1975); Kronick, P. et al. *Science.* 200:1074–1077 (1978); Molday, R. et al. *Nature.* 268:437–438 (1977); Nash, A. *Journal of Immunological Methods.* 12:149–161 (1976); Widder, K. et al. *Journal of Histochemistry and Cytochemistry.* 29:870–873 (1981); Widder, K. et al. *Clinical Immunology and Immunopathology.* 14:395–400; and Widder, K. et al. *Journal of Pharmaceutical Science.* 70 (1981).

Procedures for growing a variety of human cells on solid supports have been widely described in the patent literature, for example, in U.S. Pat. Nos. 3,717,551 (porous silica spheres), 3,778,353, 3,796,638, and 3,875,000 and 3,893,887 (roller bottles). Cultivation of fetal cells in amniocentesis has been described by Valenti, C. TISSUE CULTURE METHODS AND APPLICATIONS. New York: Academic Press, pp 617–622 (1973) and Freshney, R. CULTURE OF ANIMAL CELLS: A MANUAL OF BASIC TECHNIQUE. New York: Alan R. Liss, (1983), the entire contents of which are hereby incorporated by reference.

SUMMARY OF THE INVENTION

This invention is a method for obtaining fetal cells for diagnostic examination comprising incubating a cell suspension containing a mixture of fetal and maternal cells in the presence of separation antibody capable of preferentially binding to maternal cell antigen or to fetal cell antigen for a time sufficient to permit antibody-antigen binding to occur. The cells having separation antibody bound thereto are separated from the mixture.

The separation antibody can be an antibody binding specifically to fetal cell antigens and not significantly to maternal cell antigens or it can be an antibody binding specifically to maternal cell antigens and not significantly to fetal cell antigens. In one embodiment of this invention, the antibody is bound to an insoluble support prior to the incubation, and separation is effected by separating the insoluble support from the cell mixture following the incubation. In another embodiment, the antibody is labeled with a fluorochrome, and the fluorescent stained cells (cells to which the fluorochrome labeled antibodies are preferentially bound) are separated from the cell suspension using a cell sorter. The isolated fetal cells are then propagated to obtain a population sufficient for diagnostic examination.

DETAILED DESCRIPTION OF THE INVENTION

Amnionic fluid, being completely isolated by the placenta, contains cells which are all fetal in origin except when an abnormal condition fails to prevent entrance of maternal cells. In amniocentesis, the cells obtained from amnionic fluid are separated from the fluid and propagated to obtain a population sufficient for diagnostic examination of the fetus. Alternate sources of fetal cells have been explored, but practical difficulties have limited their application, prior to this invention.

Placental tissues which can be obtained by biopsy have been proved to be a possible source of fetal cells by H. A. Gardner et al, supra. The fetus and the placenta both originate from the fertilized ovum, and being from the same genetic source, they both contain fetal cells. The placenta is a complex organ composed of different types of trophoblasts and a variety of other fetal tissues such as stroma, endothelium and blood elements. The junctional area of the human placenta and uterus comprises an admixture of fetal and maternally derived cells. Placental samples therefore contain a mixture of fetal and maternal cells. Without their isolation, such cell samples have limited diagnostic value. Even if the placental tissue is reduced to single cells, no practical way for separating the fetal cells from the resulting mixture has been available prior to this invention.

Samples of detached cells obtained from the cervical cavity include fetal cells originating from the placenta mixed with maternal cells originating from the cervical endometrium and the placenta. If the fetal cells could be separated from the maternal cells in the mixture, they could be propagated to provide a valuable source of fetal cells for diagnostic analysis. Because they could be obtained by a procedure which would not require any penetration or disturbance of the integrity of the amnionic sac, sampling could be effected by a nurse or other suitably trained technician without the need for ultrasound monitoring of the relative position of a sampling needle and the fetus or other equivalent, complex, surgical procedure.

The cells can be obtained from the uterine cavity through the uterine canal by a variety of relatively safe procedures. A swab or other collecting tool can be inserted through the mucus plug of the uterine canal. A particularly convenient procedure for collecting these cells is described in commonly assigned, copending application Ser. No. 689,341 filed Jan. 7, 1985. The apparatus described in the application comprises a sampling probe which after being inserted through the mucus plug, can irrigate the surfaces of the uterine endometrium and placenta with a suitable medium and remove the suspended cells from the cavity. The cells can then be treated in accordance with the procedure of this invention to separate the fetal cells for propagation and examination.

In the cell separation procedure of this invention, the cells are incubated in the presence of a separation antibody. Separation antibodies can be selected which bind preferentially to antigens present in or on fetal cells and not present in or on maternal cells, or which bind preferentially to antigens present in or on maternal cells and not present in or on fetal cells. Because of this selective binding, the separation antibodies can be used to distinguish maternal cell antigen from fetal cell antigen, and consequentially, maternal cells from fetal cells. After antibody to fetal cell antigen binding has occurred, cells having separation antibody bound thereto are separated from the mixture.

The term "separation antibody", as used herein, includes both an antibody binding specifically to fetal cell antigens and not signficantly to maternal cell antigens and an antibody binding specifically to maternal cell antigens and not significantly to fetal cell antigens.

A variety of monoclonal antibodies which bind specifically to antigens which are present on the maternal cell surface and are not significantly present on the fetal cell surface have been described together with methods for their preparation by the following publications and the publications cited therein, the entire contents of which are hereby incorporated by reference. Such monoclonal antibodies are described, for example by M. Kawata et al, supra. Monoclonal antibody MB40.5 which binds with framework components HLA-A,B,C heavy chain is described together with its method of preparation by Brodsky, F. M. et al. *J.Immunol.* 128:129 (1982). Monoclonal antibody W6/32 which binds to similar antigens is described by Barnstable, C. K. et al *Cell.* 14:9 (1978). Monoclonal antibody PA2.1 which binds specifically to HLA-A2 Antigen is described by Parham, P. et al. *Nature* (Lond.). 276:397 (1978). Monoclonal antibody BBM.1 which binds with beta-2-microglobulin is described by Brodsky, M. F. et al. *Eur.J.Immunol.* 9:536 (1979). Monoclonal antibody L368 which is an anti-beta-2-m antibody when associated with HLA-A,B,C and anti-HLA-DR monoclonal antibody are described by Lampson, L. A. et al. *J. Immunol.* 125:293 (1980).

Antibodies which bind specifically to fetal cell antigens and which do not bind significantly to maternal cell antigens have also been described together with their method of preparation in the following publications and the references cited therein, the entire contents of which are hereby incorporated by reference. Monoclonal antibodies Anti-Trop-1 and Anti-Trop-2 have been described by Lipinski, et al. *Proc.Natl.Aca.-Sci.USA* 78:5147 (1981), and their binding specificity for fetal cells has been characterized by M. Kowata, et al., Supra.

In general murine hybridomo producing these antibodies can be prepared by the procedures of Kohler, G. and Milstein, C. *Nature* (London). 256:495 (1975) and clones selected for their ability to produce antibodies which bind to the selected antigen. More modern advancements in this technology are presented by Goding, J. MONOCLONAL ANTIBODIES: PRINCIPLES AND PRACTICE. London: Academic Press, (1983) and the numerous publications cited therein, the entire contents of which are hereby incorporated by reference.

The maternal or fetal antigen specific primary antibodies can be used in modified or unmodified form. For example, in the unmodified form they can be incubated with the cell sample, and secondary antibodies with separation labels can be bound therewith to facilitate separation. Alternatively, these separation antibodies can be directly coupled to a material which facilitates the selected separation step. Cells tagged with fluorescent groups can be separated with a cell sorter by standard procedures, for example. The maternal or fetal antigen specific antibody can carry a fluorescent label by means of which the cell sorter can identify the target cell conjugated with antibody. Alternatively, the primary antibody can be unmodified and a fluorescent labeled antibody which binds specifically the separation antibody can be used to bind the fetal or maternal cell with a separation label. Since monoclonal antibodies represent a single class of antibody, a fluorescent labeled secondary antibody which binds with members of that class can be used.

A preferred embodiment of this invention uses separation antibodies which have been previously bound to a surface or composition which can be physically separated from the cell mixture following the conjugation with the cell surface antigens. Such antibodies can be coupled to solid surfaces such as plastic or glass containers, wells, beads, or particles which have properties which can be used for the separation. Particularly if the separation antibody will selectively bind to fetal cells, the insoluble support must be selected so as not to reduce the viability of the cells following coupling, since the fetal cells separated by this procedure will be subsequently propagated. Coated magnetic particles can be coupled to a separation antibody as described in U.S. Pat. No. 3,970,518. Magnetic particles suitable for separating biological materials including cells are also described in U.S. Pat. Nos. 3,985,649 and 4,177,253 for example.

Antibodies have been adhered to numerous solid supports by both physical and chemical bonding. Methods for bonding antibodies to insoluble supports as described in U.S. Pat. Nos. 3,551,555, 3,553,310, 4,048,298 and RE-29,474, for example. Techniques for bonding antibodies to polystyrene supports by adsorption has been described in U.S. Pat. Nos. 3,646,346 and 4,092,408. The binding of biological materials to solid, magnetic particles is described in U.S. Pat. Nos. 3,933,997, 3,985,649, 4,177,253 and 4,297,337, for example. Coating magnetic particles with antibodies for separating selected cells from mixtures has been described in U.S. Pat. No. 3,970,518. Cell separation using coated magnetic materials is described by Antoine, J. et al. *Immunochemistry.* 15:443–452 (1978); Ghelie, V. et al. *Scand. J. Immunol.* 4:471–477 (1975); Kronick, P. et al. *Science.* 200:1074–1077 (1978); Molday, R. et al. *Nature* 268:437–438 (1977); Nash, A. *Journal of Immunological Methods.* 12:149–161 (1976); Widder, K. et al. *Journal of Histochemistry and Cytochemistry.* 29:870–873 (1981); Widder, K. et al. *Clinical Immunology and Immunopathology.* 14:395–400; and Widder, K. et al. *Journal of Pharmaceutical Science.* 70 (1981).

Procedures for coupling antibodies to insoluble glass and plastic surfaces are described in U.S. Pat. Nos. 3,551,555, 3,553,310, 4,048,298, Re-29,474, 3,646,346 and 4,092,408, for example.

A wide variety of materials can be used as an insoluble support for separating fetal cells from the cell mixture. The only limitation in selecting a support and bonding method is the ability to bind the cell antigen specific antibody to the insoluble support without significantly reducing the binding affinity for the cell antigen and the ability of the support to receive the cells without reducing cell viability. Polymers or metals which contain materials toxic to the cells are thus less effective unless the surfaces are securely coated with a sealing layer which protects cells adhering thereto. Rough and highly porous surfaces are also not preferred because if cells are to be removed from the support before propagation because of the difficulty in removing cells therefrom. Suitably inert solid surfaces are polymers such as polyethylene, polypropylene, polybutylene, silicone rubbers and silastic polymers, polystyrene and styrene graft copolymers, and similar polymers; inert inorganic materials such as glass vials, bottles, beads and particles; and other materials which are coated with non-toxic polymers or inorganic materials.

Of particular interest are functionalized polymers with non-toxic groups which can be easily bonded to antibodies such as hydroxy groups, amino groups and carboxylic acid groups. Linking antibodies to suitable reactive groups can be effected using procedures described by Ichiro chibata in IMMOBILIZED ENZYMES, New York: Halsted, (1978) and A. Cuatrecasas in *J.Bio.Chem.* 245:3059 (1970).

In one embodiment of this invention, wherein cell antigen specific antibodies of the IgG class are to be used, a particularly advantageous procedure involves the chemical bonding of anti-IgG antibody to the insoluble support using any of the procedures which do not leave toxic residues and which do not interfere with the anti-IgG antibody binding. This procedure has the advantage of permitting the coating of the support with an excess of anti-IgG antibody, a reagent which is available in substantial quantity. The less available cell antigen specific IgG antibody can then be conjugated thereto using mild, antibody sparing procedures.

Incubation of the cell sample suspension and the separation antibody is continued until the antibody-antigen binding has occurred. During this incubation, the temperature is maintained within the range required for cell propagation. A temperature of from 35° to 37° C. is usually suitable. Conjugation is usually complete at this temperature within from one to 12 hours. If secondary antibody conjugation with primary antibodies bound to the selected cell type is employed, separation of cell mixture from the primary antibody solution will be required before contacting the cells with the secondary antibody solution. Because this may not be convenient, use of separation labeled primary antibodies is preferred, either fluorescent labeled primary antibodies or primary antibodies which have been previously bonded to an insoluble support.

The cells coupled directly or indirectly with separation labels through primary and/or primary and secondary systems are separated from the mixture. Separation of fluorescent labeled cells from the mixture can be achieved using the fluorescence-activated cell sorter using the procedures described by Herzenberg et al. *Proc. Natn. Acad. Sci.* U.S.A. 76:1453–1455 (1979).

Separation of cells conjugated with insoluble supports can be achieved by separating the insoluble supports from the mixture. If the insoluble support is a magnetic bead or particle, separation can be accomplished by bringing a magnet into close proximity to a suspension of the cells, drawing the desired cells to a locus in the vicinity of the magnet, and removing the remainder of the cells from the mixture. Other suitable cell separation procedures are described by Freshney, R., supra, pp 145–158, the entire contents of which are hereby incorporated by reference.

If the insoluble support is a container, the contents can be removed by pouring the liquid from the container. Beads and other particulate supports can be filtered from the cell suspension. Precipitated materials can be separated by centrifugation or sedimentation and decanting the liquid phase away from the solid layers.

In embodiments of this invention where antibodies specific for the maternal cells such as the anti-(HLA-A,B,C antigen) antibodies are used for the separation, supports to which these antibodies are adhered are separated from the cell mixture, and the remainder of the cell mixture is retained.

In the preferred embodiments of this invention, the antibodies used for the separation are the anti-trophoblast antibodies, in particular the anti-Trop-1 or anti-Trop-2 antibodies described hereinabove. When the desired fetal trophoblast cells are conjugated to a suitable, insoluble support, the support can be removed and used as a growth supporting medium.

For propagation of the cells, the cells are suspended in a suitable nutrient medium. The cell mixture is suspended in an aqueous medium in which the fetal cells will remain viable during the incubation with the separating antibody. If the cells are collected by a procedure involving irrigating the cervical cavity, such a suitable medium can be used for the original cell sample collection. A wide variety of media are known to be suitable for propagating human cells including fetal cells. Examples of several defined media and established procedures for growing cells are presented by Freshney, R., supra, pp 67-68 and 119-128, the entire contents of which are hereby incorporated by reference. Procedures for growing fetal cells for examination are described by Epstein, C. et al. *Am. J. Hum. Genet.* 24:214-226 (1972); Golbus, M. et al. *Am. J. Obstet. Gynecol.* 118:897-905 (1974); and Pattillo, R. et al. *Cancer Research.* 28:1231 (1968) and *Science,* 159:1467 (1968). Gnerally the fetal cells are cultured as a monolayer. Valenti, C., supra, pp 617-622.

When the monolayer starts to proliferate, it is ready for chromosome analysis. The cells are examined for evidence of chromosomal abnormalities, enzyme deficiencies, and the like. Procedures for evaluating fetal cells for such conditions are described by Freshney, R., supra, pp 159-172 and Golbus, M. supra, and the references cited therein.

This invention is illustrated by the following specific, but non-limiting examples. Temperatures are in degrees centigrade unless otherwise specified.

EXAMPLE 1

Anti-trophoblast antigen binding antibodies

Antibodies which bind preferentially to fetal cells are prepared from fused murine spleen cells and SP2/0 cells prepared in accordance with the procedure of Kohler and Milstein. White BALB/c mice are immunized with a suspension of fetal tissue containing fetal trophoblast cells in three immunizations at 14 day intervals with $2 \times 10^7$ cells/mouse/injection in 0.2 ml phosphate buffered saline (PBS). Each mouse is bled by incision of the brachial artery and immersed in 70% ethanol, placed on a clean surface, and the spleen is removed aseptically. The spleen is rinsed in a Petri dish with about 10 ml of PBS/G and 20 ml of an antibiotic and antimycotic solution. The spleen are placed in a second PBS solution containing antibiotic and antimycotic, and the spleen cells are removed, centrifuged, resuspended in PBS/G and recentrifuged.

The separated spleen cells resuspended in PBS/G are combined with SP2/0 cells in a 1:1 ratio in a 50 ml tube, centrifuged, and 1-2 ml of PEG (mw 1300-1600) at 37° C. is added over 1.5 min to the pellet with stirring. The tube is placed in a 37° C. waterbath for 90 sec, swirling the cells. The PEG is slowly diluted by adding PBS/G dropwise over 1 min, adding 5 ml of PBS/G slowly over 2 minutes, adding 30 ml of PBS/G over 5 minutes, and then completely filling the tube with PBS/G, letting the final mixture stand for 5 min.

The suspension is centrfuged ($200 \times g$) for 10 minutes, discarding the supernatant. The pellet cells are blasted with 50 ml of RPMI medium containing 10% fetal calf serum with an autopipettor, and the cell suspension is centrifuged ($200 \times g$) for 10 min. The cells are then gently resuspended in HAT media by blasting the pellet with media from an autopipettor. Sufficient HAT media is added to dilute the pellet to a concentration of $10^6$ spleen cells per ml. The cells are plated at 100 microliters per well into 96 well microtiter plates.

In this manner, a spleen having approximately $2 \times 10^8$ cells is resuspended after fusion in 200 ml HAT medium and distributed over approximately 2000 wells (20 microtiter plates). The plates are incubated at 37° C. in a humidified incubator containing 5% $CO_2$ and 95% air.

Six weeks following fusion, supernates are removed from wells with confluent growth. Samples are tested for antibody binding to fetal trophoblast cells using the following procedure.

1. 5 Micron frozen fetal tissue sections including fetal trophoblast cells are placed on formol-gelatin coated slides prepared by dipping slides in an aqueous solution containing 1.0% formaline and 0.5% gelatin and air drying them.

2. The slides are washed once for 30 min at 37° C. and once for 30 min at room temperature in phosphate buffered saline (PBS), pH 7.2, containing 0.1% bovine serum albumin (BSA).

3. The slides are dipped once in PBS/BSA in a coplin jar and covered with 50-70 microliters of normal goat serum (NGS) at a 1:10 dilution and incubated at room temperature for 20-30 min in a moist chamber.

4. The slides are then covered with 50-70 microliters of an appropriate dilution of the cell culture supernatant being screened for antibody activity, and incubated for 20-30 min at room temperature.

5. After removing the excess supernatant, the slides are dipped in a coplin jar of PBS/BSA and covered with 50-70 microliters of an appropriate dilution of fluorescein isothiocyanate labelled goat anti-(human Ig) immunoglobulin (TAGO) and incubated for 20-30 minutes at room temperature in the dark.

6. The slides are washed by dipping in a coplin jar with PBS/BSA, dipped once in deionized water and covered with glass coverslips with PBS/glycerine (1:10).

7. The slides are examined under a fluorescent microscope to determine if troplablast cells are highlighted by fluorescene.

In this manner the wells were screened, and wells showing the presence of antibodies binding preferentially to fetal trophoblast cells are selected for expansion and further characterization. Cells from the selected wells are expanded in HAT medium, replated, incubated and rescreened using standard cloning procedures until wells containing single clones of hybridoma cells which are producing fetal trophoblast cell antigen binding antibodies are obtained.

EXAMPLE 2

Fluorescein labeled anti-trophoblast antibodies

The anti-trophoblast antibody prepared in accordance with the procedures of Example 1 is reacted with fluorescein isothiocyanate according to the procedure of R. Mishell et al, supra, pp 293-298. The antibody solution is freed of ammonium ions by dialysis against 0.15M NaCl (3 changes in 3 days), the dialyzed against 0.05M bicarbonate-buffered saline, pH 8.5 for 4-5 hours, followed by a dialysis for 2 hours against 0.05M bicarbonate-buffered saline, pH 9.2. All dialysis is conducted at 4° C.

The antibody is coupled to the fluorescein molecule by dialyzing the antibody solution against a solution of 100 micrograms of fluorescein isothiocyanate prepared by dissolving the fluorescein isothiocyanate in 0.5M bicarbonate-buffered saline, pH 9.2, to a final concentration of 8-10 mg/ml. The volume of fluorescein isothiocyanate solution is 10 times the volume of the antibody solution. This dialysis is conducted at 4 degrees C. for 14-16 hours. The reaction is stopped by changing the dialysis buffer to 0.02M phosphate-buffered saline, pH 7.0, at 4 degrees c. The solution is dialyzed for 2-3 hours against this buffer.

The fluorescein-antibody conjugate is purified by chromatography on Sephadex (pharmacia fine chemicals) G-25 in 0.02M phosphate-buffered saline, pH 7.0, to remove free fluorescein from the conjugates. The bed is at least 10 times the volume of the conjugate solution. Further purification is achieved by dialyzing the conjugate solution against 0.0175M phosphate buffer, pH 6.5; centrifuging (10,000×g, 10 min.) to remove any precipitate and applying supernatant to a 10 cm DEAE column equilibrated with 0.0175M phosphate buffer, pH 6.5; eluting fractions with increasingly modified antibody by steps of 0.1M, 0.1 M, 0.2M, and 0.25M NaCl in 0.0175M phosphate buffer, pH 6.5; and concentrating fractions with 50% saturated ammonium sulfate solution, and dialyzing against buffered phosphate solution.

EXAMPLE 3

Magnetic microspheres coupled to anti-trophoblast antibodies

Magnetic microspheres are made by emulsifying human serum albumin and magnetic in oil followed by heat treatment at 135° C. Staphylococcal Protein A is then covalently bonded to the microspheres according to the procedures of B. Mishell et al, supra, pp 303-304. A 0.1 M phosphate buffer solution containing 5 mg Staphylococcal Protein A and the microspheres, pH 6.8, is slowly stirred while 0.1 ml of aqueous 0.5% glutaraldehyde is added at room temperature. The reaction is continued for 1 hour and terminated by separating the magnetic particles from the solution and resuspending them in 0.05M phosphate buffer, pH 7.5.

The Staphylococcal Protein A coupled microspheres are mixed incubated with a phosphate buffered solution, pH 7.2, containing the anti-trophoblast antibodies of Example 1 for 8 hours. The microspheres are then separated from the solution and resuspended in phosphate buffer solution, pH 7.2.

EXAMPLE 4

Magnetic particles coupled to anti-trophoblast antibodies

Magnetite particles are silanized by the procedure of U.S. Pat. No. 4,177,253 by mixing 1 gm of magnetite to 100 ml of a 10 w/v % solution of omega-glycidoxypropyltrimethoxy silane in dry toluene. The mixture is refluxed for 8 hours, and the silanized magnetite is filtered off, and washed with toluene and then acetone.

A 0.4 gm portion of the silanized magnetite is added to one ml of a 5% solution of anti-trophoblast antibody prepared in accordance with the procedure of Example 1, and the mixture is retained at room temperature for 48 hours. The magnetite is then washed with 0.5M aqueous sodium carbonate solution, then with 0.1M phthalate solution in 1M aqueous sodium chloride at pH 3.0, and then in 0.1M trimethoxyaminoethane in 0.5M aqueous ethanolamine at pH 7.8.

EXAMPLE 5

Fetal cell separation

An aqueous solution (1 ml) of isotonic saline, pH 6.8, containing a mixture of fetal cells and maternal cells is mixed with 0.1 ml of the fluorescein labeled antibody solution of Example 2 and incubated for 12 hours at 37° C. The cells are then separated from the solution by centrifugation at 10,000 rph for 15 minutes and resuspended in isotonic saline, pH 6.8.

The cells showing fluorescence are then separated using a cell sorter according to the procedure of Herzenberg, L. et al, supra, p 221, to yield a suspension of fetal cells free from maternal cells.

EXAMPLE 6

Separation of fetal cells with magnetic beads

A 0.1 mg portion of the magnetic beads coupled with anti-trophoblast antibodies of Example 3 is mixed with 10 ml of an isotonic saline solution, pH 6.8, containing a mixture of fetal cells and maternal cells, and incubated for 8 hours at 37° C. The microspheres having fetal cells bound thereto are removed from the cell mixture with a magnetic and resuspended in isotonic saline solution, pH 6.8.

EXAMPLE 7

Cultivation of fetal cells

The magnetic microspheres coated with fetal cells obtained in Example 6 are suspended in a nutrient media comprising Waymouth MB 752 (30 v %)
Geys DDS (70 v %)
Placental cord serum (10 v %)

The suspension is incubated in a 37° C. water bath for 2 weeks. Cell proliferation is then evident. The cells are removed from the microspheres by mild agitation, the microspheres removed from the suspension with a magnet, and the cells concentrated by centrifuging (10,000 rpm for 15 min). The cells are then examined for chromosomal abnormalities according to the procedures described by M. Globus, et al, supra.

EXAMPLE 8

Cultivation of fetal cells

The fetal cells obtained according to the procedure of Example 2 are resuspended in a nutrient media comprising Waymouth MB 752 (30 v %)
Geys DDS (70 v %)
Placental cord serum (10 v %)

The suspension is incubated in a 37° C. water bath for 2 weeks. Cell proliferation is then evident. The cells are then examined for chromosomal abnormalities according to the procedures described by M. Globus, et al, supra.

The Invention claimed is:

1. A method for concentrating fetal cells for diagnostic examination comprising
   (a) removing detached cells from the uterine cavity during pregnancy;
   (b) incubating the detached cells in the presence of at least one separation antibody which preferentially binds to fetal cells among the detached cells and which does not preferentially bind to maternal cells among the detached cells; and
   (c) separating cells having said separation antibody bound thereto from cells not having said separation antibody bound thereto.

2. The method of claim 1 wherein the cells are incubated in the presence of a separation antibody adhered to an insoluble support, and cell separation is effected following conjugation by physically separating the insoluble support with the fetal cells adhering thereto from the cell mixture.

3. The method of claim 1 wherein the separation antibody is labeled with a fluorescent label, and the fetal cells having the separation antibody adhered thereto are separated from the cells not having separated antibody adhered thereto with a cell sorter.

4. A method for concentrating fetal cells for diagnostic examination comprising
   (a) removing detached cells from the unterine cavity during pregnancy;
   (b) incubating the detached cells in the presence of at least one separation antibody which preferentially binds to maternal cells among the detached cells and which does not preferentially bind to fetal cells among the detached cells; and
   (c) separating cells having said separation antibody bound thereto from cells not having said separation antibody bound thereto.

5. The method of claim 4 wherein the cells are incubated in the presence of a separation antibody adhered to an insoluble support, and cell separation is effected following conjugation by physically separating the insoluble support with the maternal cells adhering thereto from the cell mixture.

6. The method of claim 4 wherein the separation antibody is labeled with a fluorescent label, and the maternal cells having the separation antibody adhered thereto are separated from the cells not having separation antibody adhered thereto with a cell sorter.

* * * * *